United States Patent
Klaas et al.

(10) Patent No.: US 6,593,376 B1
(45) Date of Patent: Jul. 15, 2003

(54) AMPHIPHILIC COMPOUNDS WITH AT LEAST TWO HYDROPHILIC AND AT LEAST TWO HYDROPHOBIC GROUPS ON A DI-, OLIGO- OR POLYENE BASE

(75) Inventors: Mark Rüsch gen. Klaas, Münster (DE); Klaus Kwetkat, Bergkamen (DE); Siegfried Warwel, Aachen (DE)

(73) Assignee: SASOL Germany GmbH, Hamburg (DE)

(*) Notice: Subject to any disclaimer, the term of this patent is extended or adjusted under 35 U.S.C. 154(b) by 0 days.

(21) Appl. No.: 09/402,601

(22) PCT Filed: Mar. 20, 1998

(86) PCT No.: PCT/EP98/01633

§ 371 (c)(1), (2), (4) Date: Dec. 30, 1999

(87) PCT Pub. No.: WO98/47865

PCT Pub. Date: Oct. 29, 1998

(30) Foreign Application Priority Data

Apr. 24, 1997 (DE) .......................... 197 17 264

(51) Int. Cl.[7] ................ B01F 17/00; C07C 305/10; C07C 43/11; C07C 69/34; C07F 9/09
(52) U.S. Cl. .................. 516/56; 516/58; 516/64; 516/75; 516/907; 516/909; 516/913; 516/919; 558/24; 558/26; 558/70; 558/114; 562/8; 562/20; 562/22; 562/36; 562/583; 562/512.4; 568/619; 568/679; 560/149
(58) Field of Search .................. 516/58, 56, 64, 516/75, 907, 909, 913, 919; 558/24, 26, 70, 114; 568/679, 619; 562/36, 8, 20, 22, 583, 512.4; 549/529; 560/149

(56) References Cited

U.S. PATENT DOCUMENTS 2,692,892 A * 10/1954 Hillyer et al. ............. 558/92
2,714,605 A * 8/1955 Jones ........................ 558/24
3,274,220 A * 9/1966 Budde ...................... 562/583
5,008,338 A * 4/1991 Riddick et al. ............ 568/679
5,160,450 A * 11/1992 Okahara et al. ........... 558/26
5,237,080 A * 8/1993 Daute et al. ............... 554/213
5,510,516 A * 4/1996 Caubere et al. ........... 560/220

FOREIGN PATENT DOCUMENTS

| AU | 692604 | 6/1996 |
| JP | 1304033 | 12/1989 |
| JP | 4124165 | 4/1992 |
| WO | WO97/09304 | 3/1997 |

OTHER PUBLICATIONS

R. Zana and Y. Talmon, "Dependence of Aggregate Morphology on Structure of Dimeric Surfactants." Nature 362, Mar. 18, 1993, pp. 228–230.

E. Alami, G. Beinert, P. Marie, and R. Zana, "Alkanediyl-1-alpha,omega-bis(dimethylalkylammonium bromide) Surfactants. 3. Behavior at the Air–Water Interface." Langmuir 9, 1993, pp. 1465–1467, month unknown.

* cited by examiner

Primary Examiner—Daniel S. Metzmaier
(74) Attorney, Agent, or Firm—Browning Bushman P.C.

(57) ABSTRACT

A process for preparing amphiphilic compounds having at least two hydrophilic and at least two hydrophobic groups by reacting an olefinic substrate having at least two double bonds with an organic hydroperoxide to form an oxirane ring, opening, the oxirane ring with an alcohol in the presence of a catalyst system comprising a molybdenum compound as a first catalyst component and a second catalyst component selected from the group consisting of boron trifluoride, alumina, 1,8-diazabicyclo-(5.4.0)-undec-7-ene, 1,4-diazabicyclo-(2,2,2)-octane.

21 Claims, No Drawings

AMPHIPHILIC COMPOUNDS WITH AT LEAST TWO HYDROPHILIC AND AT LEAST TWO HYDROPHOBIC GROUPS ON A DI-, OLIGO- OR POLYENE BASE

BACKGROUND OF THE INVENTION

1. Field of the Invention

This invention relates to amphiphilic compounds with at least, two hydrophilic and at least two hydrophobic groups based on di-, oligo-, or polyenes and also to a process for their preparation, and to their use as dispersants, emulsifiers, demulsifiers, as auxiliaries in ore mining, metal working, surface finishing, plastics production or processing, as auxiliaries for the application of crop protectants, as adjuvants in medical applications, as textile auxiliaries, as auxiliaries for the cleaning and washing of textiles, as auxiliaries for the cleaning of hard surfaces, and as auxiliaries for the cleaning and washing of skin and hair.

2. Description of the Related Art

A wide variety of anionic, cationic, nonionic, and zwitterionic compounds are known as amphiphilic substances. By far the most of these substances consist of a hydrophilic head group and at least one hydrophobic moiety.

With the amphiphilic substances there is a need, for ecological reasons, for example regarding the reduction in packaging and transportation expenditure, to achieve an increasingly greater effect per mass of substance employed. Since only little optimization can be achieved by mixing amphiphilic substances, novel amphiphilic substances with greater efficiencies are required. In particular, there is a need for substances having lower critical micelle concentrations and/or lower surface and interfacial tensions in order to significantly reduce the amount of active substance used.

Initial approaches to solving this problem by doubling part of the structure (hydrophilic head group, hydrophobic group) have already been disclosed. For example, it is known to prepare cationic surface-active compounds by addition of long-chain alkyl halides to permethylated alkylene diamines [see Zana, R., Benrraou, M., Rueff, R., *Langmuir*, 7 (1991), p. 1072; Zana, R., Talmon, Y., *Nature*, 362 (1993), p. 228; Alami, E., Beinert, G., Marie, P., Zana, R., *Langmuir*, 9 (1993), p. 1465].

Anionic surface-active compounds with at least two hydrophilic and at least two hydrophobic groups have to date been prepared only on the basis of diglycidyl ethers (cf. U.S. Pat. No. 5,160,450, JP 01 304 033, JP 4 124 165). However, diglycidyl ethers are regarded as toxicologically objectionable and are rather expensive. Furthermore, epichlorohydrin is used for their preparation, which results in large amounts of residues so that said compounds are no longer in accord with the times both in ecotoxicological and economic aspects.

SUMMARY OF THE INVENTION

Therefore, it was an object of the present invention to prepare amphiphilic compounds which have at least two hydrophilic and at least two, hydrophobic groups, wherein the amphiphilic compounds have very high efficiencies, relative to the feed quantity, and, furthermore, can be prepared from raw materials which are technically readily available without producing large amounts of undesirable by-products.

DESCRIPTION OF THE PREFERRED EMBODIMENTS

According to the present invention, the problem is solved by providing amphiphilic compounds based on di-, oligo-, or polyenes.

The amphiphilic compounds of this invention are compounds which, when alkylene dienes are used, typically correspond to the general formulae I and II. The result is analogous for the reaction of a plurality of double bonds.

Formula I

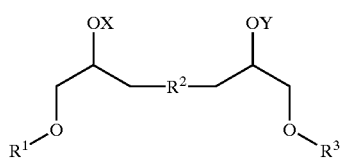

Formula I

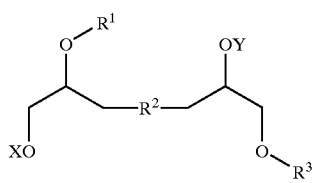

Formula II

The invention therefore relates to amphiphilic compounds of the general formulae I and II or, on reaction of a plurality of double bonds, analogous structures.

Formula I

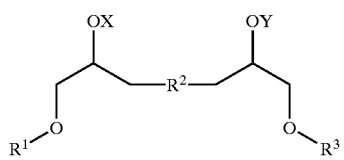

Formula I

Formula II

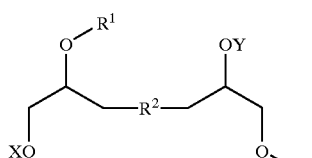

Formula II where $R^1$ and $R^3$, independently of one another, represent an unbranched or branched, saturated hydrocarbon radical or a partially fluorinated or perfluorinated hydrocarbon radical having 1 to 22, preferably 6 to 18, carbon atoms, $R^2$ is a spacer, and X and Y, independently of one another, are substituents of the formula XV $$-(C_2H_4O)_\alpha(C_3H_6O)_\beta H \qquad (XV)$$

where $\alpha=0$ to 50, preferably $\alpha=0$ to 15,
$\beta=0$ to 60, preferably $\beta=0$ to 10, and
$\alpha+\beta=1$ to 100, preferably $\alpha+\beta=1$ to 20, or of the formula XVI $$-(C_2H_4O)_\gamma(C_3H_6O)_\delta-FR \qquad (XVI)$$

where $\gamma=0$ to 20, preferably $\gamma=0$ to 8, $\delta=0$ to 20, preferably $\delta=0$ to 12, and $\gamma+\delta=0$ to 40, preferably $\gamma+\delta=0$ to 20, and FR is a functional radical $-CH_2-COOM$, $-SO_3M$, $-P(O)(OM)_2$, $-C_3H_6-SO_3M$, or $-O-C(O)-C_2H_3(SO_3M)-CO_2M'$ with M, M' representing alkali, ammonium-, substituted ammonium-, or ½ alkaline earth metal ion, and where the alkoxide units are incorporated randomly or blockwise, and the sequence is arbitrary.

Examples of the substituents $R^1$ and $R^3$ include the radicals methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-henicosyl, n-docosyl, and branched-chain isomers thereof as well as their partially fluorinated or perfluorinated equivalents.

$R^2$ is a spacer consisting of an unbranched or branched chain with 2 to 30 carbon atoms which comprises 0 to 10 oxygen, 0 to 10 nitrogen, and 0 to 3 sulfur atoms and which has 0 to 10 functional side groups, such as carbonyl, carboxyl, amino and/or acylamino groups.

The spacer $R^2$ represents in particular unbranched or branched alkylene chains as a body

  (III)

where a=2 to 18, preferably a=2 to 6;

alicyclic compounds of the formula IV as a body

  (IV)

where each f and g, independently of one another, is equal to from 1 to 6;

or of the formula V

-3(4),8(9)-di(methylene)-tricyclo[5.2.1.0$^{2.6}$]decane-  (V)

optionally as a body, substituted aromatics of the formula VI

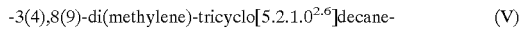  (VI)

or of the formula VII

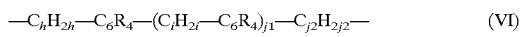  (VII)

where each h, j, $j_1$, and $j_2$, independently of one another, is equal to from 0 to 8, and i is equal to from 0 to 8, and each R in the formulae VI and VII, independently of one another, is equal to H or $C_1-$ to $C_6$-alkyl;

a chain with functional side groups, particularly carbonyl, carboxyl, amino and/or acylamino groups.

The spacer $R^2$ furthermore comprises in each case from 0 to 10, preferably from 1 to 5, oxygen and/or nitrogen atoms and/or from 0 to 3 sulfur atoms.

Thus, $R^2$ furthermore represents in particular a compound of the formula VIII

  (VIII)

where each k and l, independently of one another, is equal to from 0 to 8, each R, independently of one another, is equal to H or $C_1-$ to $C_6$-alkyl, x is equal to 6 and y is equal to 4, or x is equal to 10 and y is equal to 6, or x is equal to 14 and y is equal to 8, and $Z=O, CO, NH, NR^1, N-C(O)R^1, SO_2$ or of the formula IX $-CH_2-CH(OCH_2CH(OX)-R^1)-CH_2-$ or an isomer  (IX)

or 2,2'-methylene-bis-(1,3-dioxolane-5-methylene)-, or acetals, particularly diacetals of dialdehydes and di-, oligo-, or polyols, wherein $R^1$ is a hydrocarbon radical having 1 to 22 carbon atoms;

a compound of the formula X

  (X)

where m=1 to 4, n=2 to 4, p=1 to 20, preferably p=1 to 4, and q=1 to 4, wherein mixed alkoxide units may also be present and if that is the case, the sequence of said alkoxide units is arbitrary;

a compound of the formula XI

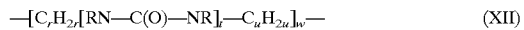  (XI)

or of the formula XII

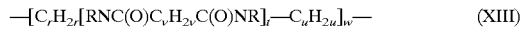  (XII)

or of the formula XIII

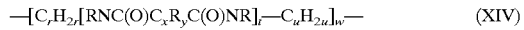  (XIII)

or of the formula XIV

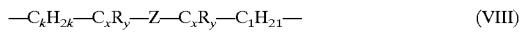  (XIV)

where r=2 to 4, s=2 to 4, t=1 to 20, preferably t=1 to 4, u=2 to 4, v=0 to 12, w=1 to 6, x=6, and y=4, or x=10 and y=6, or x=14 and y=8, and R, independently of one another, is equal to H or $C_1-$ to $C_6$-alkyl.

X and Y, independently gf one another, are substituents of the formula XV

  (XV)

where $\alpha=0$ to 50, preferably $\alpha=0$ to 15, $\beta=0$ to 60, preferably $\beta=0$ to 10, $\alpha+\beta=1$ to 100, preferably $\alpha+\beta=1$ to 20;

or substituents of the formula XVI

  (XVI)

where $\gamma=0$ to 20, preferably $\gamma=0$ to 8, $\delta=0$ to 20, preferably $\gamma=0$ to 12, and $\gamma+\delta=0$ to 40, preferably $\gamma+\delta=0$ to 20, and FR represents a functional radical $-CH_2-COOM$, $-SO_3M$, $-P(O)(OM)_2$, $-C_3H_6-SO_3M$, or $-C(O)-C_2H_3(SO_3M)-CO_2M'$ with M, M' representing alkali, ammonium, substituted ammonium, or ½ alkaline earth metal, and where the alkoxide units are incorporated randomly or blockwise and the sequence is arbitrary.

In each case the degree of alkoxylation is an average value which can be any desired value, even a non-integral one, within the specified limits.

A further object of the present invention is a process for preparing the amphiphilic compounds described hereinabove, wherein the preparation comprises two steps.

In each case there are obtained mixtures of said compounds because the opening of the epoxides formed during the reaction according to this invention takes place with selectivities of only 50 to 90%, preferably 70 to 80%, from the less substituted side.

The first step comprises the preparation of hydroxy ethers (X, Y=H, formula I or II and analogous structures) by reacting di- or oligoenes, which may be cyclic or acyclic, with organic hydroperoxides, ROOH, as oxidants and opening of the resultant oxirane ring by mono- or polyhydric alcohols in the presence of homogeneous or heterogeneous molybdenum compounds as a first catalyst component and boron trifluoride, as a stabilized complex, or of an alumina or 1,8-diaza-bicyclo-[5.4.0]-undec-7-ene or 1,4-diazabicyclo-[2.2.2]-octane as a second catalyst component and use of mono- or polyhydric alcohols as a nucleophile and simultaneously as a solvent, the use of other solvents not being precluded.

In a second step according to this invention the resultant di- or oligools are converted into nonionic surfactants with the aid of alkoxylating agents, or are converted, preceded by alkoxylation or directly, into anionic, amphiphilic compounds. This can be achieved for example by oxidizing the compounds referred to hereinabove with sulfur trioxide/inert gas, oleum, chlorosulfonic acid or sulfamic acid, with polyphosphoric acid, with a haloacetic acid or with oxygen in the presence of a TEMPO derivative (TEMPO derivatives are derivatives of 2,2',6,6'-tetramethylpiperidine oxides), by reaction with a sultone, a taurine, or with maleic anhydride and sodium bisulfite and, in each case, by subsequent neutralization with aqueous alkali or alkaline earth metal hydroxides or aqueous ammonia or alkanol amines. Optionally, the products can be bleached in aqueous solution with hydrogen peroxide (0.1 to 2.0% based on solid).

Although the individual components of the reaction are known, it is surprising that they can be combined in a 'one-pot process' and that the α-hydroxy ether is formed selectively in the reaction. The catalyst components do not adversely affect one another, and it can in fact be observed that $BF_3$ enhances the activity of the molybdenum catalyst for the epoxidation.

Suitable epoxidation catalyst components for the process according to the invention are molybdenum compounds which are soluble in the reaction mixture, such as molybdenum acetylacetonate, $MoO_2(acac)_2$, or molybdenum hexacarbonyl, $Mo(CO)_6$. Also suitable is molybdenum oxide on a catalyst carrier as a heterogeneous catalyst. Appropriate catalyst carriers are amorphous aluminosilicates or zeolites with high Lewis acidity. The molybdenum catalyst is employed in quantities of from 0.01 to 5 mol %, preferably 0.25 to 2 mol %, most preferably 0.5 to 1.0 mol %, based on the C=C double bond to be oxidized.

According to the invention, it is possible to employ as a second catalyst component boron trifluoride or adducts, such as the etherate or the methanolate. Also suitable are alumina, $Al_2O_3$, and the basic compounds 1,8-diazabicyclo-[5.4.0]-undec-7-ene or 1,4-diazabicyclo-[2.2.2]-octane. These catalyst components are employed in quantities of from 0.01 to 5 mol %, preferably 0.25 to 2.0 mol %, most preferably 0.5 to 1.0 mol %, based on the C=C double bond to be oxidized.

The olefinic substrates which can be employed are terminally and/or internally di- or polyunsaturated aliphatic, cyclic, or acyclic hydrocarbons or fatty acids and their esters. Expediently, the alcohol component in the fatty acid esters should be the same as the alcohol used in order that the transesterification which is likewise catalyzed does not yield undesirable product mixtures.

It is possible to employ for the process according to the invention mono- or polyhydric alcohols with primary, secondary, or tertiary hydroxyl groups and any desired chain length. If compounds of the formula II are to be prepared, only primary hydroxyl groups should be employed for the etherification in order to avoid undesirable product mixtures. The alcohol and the olefinic substrate may comprise further functional groups, such as ester groups, carbonyl carbons, amides, ethers, as long as said groups are unable to compete effectively as nucleophiles in the reaction.

Suitable oxidants for the process according to the invention include commercially available hydroperoxides, such as tert-butyl hydroperoxide; or cumene hydroperoxide. The oxidant is employed at a ratio of 1.0:1.3, based on the double bond equivalents to be oxidized.

The reaction in the process according to the invention can be carried out at temperatures starting at the melting point of the reaction mixture and ending at the boiling point of the reaction mixture. The reaction is furthermore preferably carried out under an inert gas atmosphere and with anhydrous reagents. For the reaction, the catalyst components and alcohol plus olefin are mixed and heated to the reaction temperature. The hydroperoxide is then metered in slowly. After completion of the reaction, the catalyst components can be filtered off and reused (the simplest case, i.e. when both are heterogeneous), or they must be removed from the product with water. The resultant α-hydroxy ethers can generally be purified by distillation, but this is often unnecessary.

The amphiphilic compounds of the present invention are mostly superior by their extremely low critical micelle concentrations (CMC) and very low surface/interfacial tensions, e.g. in relation to: paraffin. These characteristics are due to the special structures of the compounds, namely at least two hydrophilic groups and at least two hydrophobic ones. Furthermore, most of said compounds have rather high hydrophilic suspending power and are exceptionally mild on the skin. Some of them are extremely rapid wetting agents.

The amphiphilic compounds of this invention are particularly useful as emulsifiers, demulsifiers, detergents, dispersants, and hydrotropes or cryptans (in the case of cyclic compounds) in industrial and domestic applications.

The instant invention furthermore relates to the use of the amphiphilic compounds in the areas of ore mining, metal working, surface finishing, plastics production and processing, cosmetics, medicine, food processing and preparation, and as auxiliaries for the application of crop protectants, and adjuvants in medical applications, as textile auxiliaries, as auxiliaries for the cleaning and washing of textiles, as auxiliaries for the cleaning of hard surfaces and as auxiliaries for the cleaning and washing of skin and hair.

Said compounds can be combined with any customary anionic, nonionic, cationic, and ampholytic surface-active substances. Examples of nonionic surface-active substances suitable for said combinations include fatty acid glycerides, fatty acid polyglycerides, fatty acid esters, ethoxylates of higher alcohols, polyoxyethylene fatty acid glycerides, polyoxyethylene propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkyl amines, alkanol amines, alkylamine oxides, protein hydrolyzate derivatives, hydroxy mixed ethers, alkyl polyglycosides, and alkyl glucamides.

Examples of anionic surface-active substances useful for said combinations include soaps, ether carboxylic acids and salts thereof, alkyl sulfonates, α-olefin sulfonates, sulfonates of higher fatty acid esters, higher alcohol sulfates, alcohol ether sulfates, hydroxy mixed ether sulfates, phosphate ester salts, taurides, isethionates, linear alkyl benzene sulfonates, alkylaryl sulfonates, polyoxyethylene fatty acid amide sulfates, and acylamino acid salts.

Examples of conventional cationic surface-active substances suitable for said combinations include alkyltrimethyl ammonium salts, dialkyldimethyl ammonium salts, alkyldimethylbenzyl ammonium salts, alkyl pyridinium salts, alkylisoquinolinium salts, benzethonium chlorides, and cationic acylamino acid derivatives.

Examples of ampholytic surface-active substances useful for said combinations include amino acids, betaines, sulfobetaines, imidazoline derivatives, soybean oil lipids, and lecithin.

Furthermore, the amphiphilic compounds of the present invention may also be combined with each other.

In addition, any commonly used additives may be added to the amphiphilic compounds of the invention. Such additives are specifically selected for a formulation and generally comprise inorganic salts, such as sodium chloride and sodium sulfate, builders, hydrotropes, such as cumene sulfonate, UV absorbers, fabric softeners, chelating agents, viscosity modifiers, fragrances etc.

The present invention will be further described with reference to the following non-limiting example.

EXAMPLE

Epoxidation and Ring Opening
Preparation of Dibutoxyoctanediol 0.05 mol of 1,7-octadiene (5.9 g) and 1 mmol of MoO$_2$(acac)$_2$ (326 mg) were dissolved in 60 ml of anhydrous 1-butanol, a spatula tip of dry molecular sieves (4 Å) was added, and the mixture was heated to 90° C. Then 0.15 ml of BF3 etherate (≈1 mmol) was added and 0.12 mol of anhydrous tert-butyl hydroperoxide (5M in decane, 24 ml) was added dropwise during 30 minutes. The mixture was allowed to further react for 16 hours. After cooling, acidification with dilute hydrochloric acid and taking up in ether, the organic phase was washed with water. The remaining crude product was dried over Na$_2$SO$_4$ and subjected to gas chromatographic analysis. The amounts of products formed were determined quantitatively after addition of a GC standard (ethyl heptanoate) and conversion of the free carboxylic acids into the corresponding methyl esters using CH$_2$N$_2$, while taking into account the correction factors previously determined on pure substances. Dibutoxyoctanediol yield: 49% of theoretical, based on 1,7-octadiene (3 isomers) (the content of the by-products epoxybutoxyoctanol, diepoxyoctane, butoxyoctenol, and butoxyoctanetriol was as low as <5%).

Sulfation

To a mixture of 61.3 g of chlorosulfonic acid and 31.8 g of acetic acid there were added dropwise 49.6 g of the diol (prepared as described hereinabove) in 200 ml of dichloromethane. During the addition the temperature was not allowed to exceed 5° C. The mixture was then stirred for three hours at room temperature after which time the diol mixture was found to be completely reacted (thin-layer chromatography). The mixture was neutralized with 2N sodium carbonate solution and diluted with saturated sodium bicarbonate solution. The product is extracted with n-butanol. Then the alcohol is removed. The purity is checked by thin-layer chromatography and NMR. Yield: 70.3 g (80% of theoretical), purity: 90% (isomers mixture).

What is claimed is:
1. A one-stage process for preparing amphiphilic compounds corresponding to the following formulas I and II:

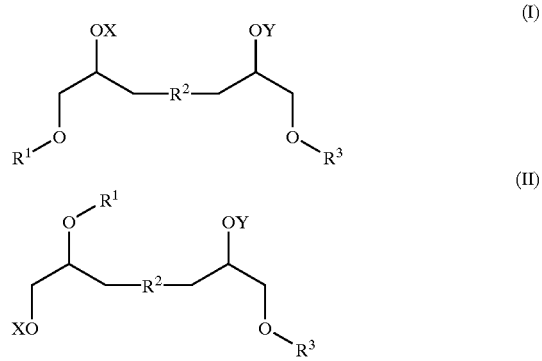

comprising oxidizing compounds having hydrocarbyl groups with at least two double bonds with an organic peroxide to form a compound having an oxirane ring, opening said oxirane ring with an alcohol in the presence of a catalyst system comprising a molybdenum compound as a first catalyst component and a second catalyst component selected from the class consisting of boron trifluoride, alumina, 1,8-diazabicyclo-(5.4.0)-undec-7-ene, and 1,4-diazabicyclo-(2.2.2)-octane, wherein $R^1$ and $R^3$, independently of one another, are selected from the group consisting of:

(A) unbranched saturated hydrocarbon radicals having from 1 to 22 carbon atoms,
(B) branched saturated hydrocarbon radicals having from 1 to 22 carbon atoms,
(C) partially fluorinated derivatives of (A),
(D) partially fluorinated derivatives of (B),
(E) perfluorinated derivatives of (A),
(F) perfluorinated derivatives of (B), and mixtures thereof;

$R^2$ is a spacer selected from the group consisting of:
(i) an unbranched or branched alkylene chain of formula III

wherein a is 2 to 18,
(ii) alicyclic compounds of formula IV

wherein f and g are independently from 1 to 6,
(iii) a grouping of formula V

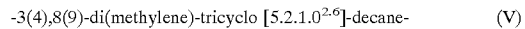

(iv) a grouping of formula VI

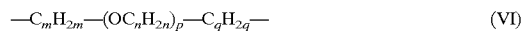

wherein m is 1 to 4, n is 2 to 4, p is 1 to 20, q is 1 to 4 and wherein, optionally, the alkoxide units are mixed alkoxide units, in any arbitrary sequence are present in the group, X and Y, independently of one another, are selected from the group consisting of:
substituents of the formula XV:

wherein α=0 to 50, β=0 to 60, and α+β=1 to 100; and substituents of the formula XVI:

—(C₂H₄O)<sub>γ</sub>(C₃H₆O)<sub>δ</sub>—FR    (XVI)

wherein γ=0 to 20, δ=0 to 20, and γ+δ=0 to 40, and FR represents a functional radical selected from the group consisting of —CH₂COOM, —SO₃M, —P(O)(OM)₂, —C₃H₆—SO₃M, or —C(O)—C₂H₃(SO₃M)—CO₂M', and M, M' are alkali, ammonium, alkanol ammonium, or ½ alkaline earth metal.

2. A process as claimed in claim 1, wherein R¹ and R³ contain from 6 to 18 carbon atoms.

3. A process as claimed in claim 1 or 2, wherein an alcohol is employed as a solvent.

4. A process as claimed in claim 1 or 2, wherein water is excluded.

5. A process as claimed in claim 1 or 2, wherein said molybdenum compound is soluble in the reaction mixture.

6. A process as claimed in claim 1 or 2, wherein said molybdenum compound is MoO₂(acac)₂ or Mo(CO)₆.

7. A process as claimed in claim 1 or 2, wherein said molybdenum compound is molybdenum oxide on a catalyst carrier.

8. A process as claimed in claim 7, wherein said catalyst carrier is selected from the group consisting of amorphous aluminosilicates and zeolites.

9. A process for preparing amphiphilic compounds, comprising:
preparing hydroxyethers of the formula:

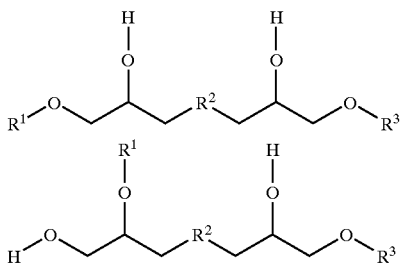

wherein
R¹ and R³ are selected from the group consisting of:
(A) unbranched saturated hydrocarbon radicals having from 1 to 22 carbon atoms,
(B) branched saturated hydrocarbon radicals having from 1 to 22 carbon atoms,
(C) partially fluorinated derivatives of (A),
(D) partially fluorinated derivatives of (B),
(E) perfluorinated derivatives of (A),
(F) perfluorinated derivatives of (B), and mixtures thereof;
R² is a spacer selected from the group consisting of:
(v) an unbranched or branched alkylene chain of formula III —C<sub>a</sub>H<sub>2a</sub>—    (III)

wherein a is 2 to 18,
(vi) alicyclic compounds of formula IV

—C<sub>f</sub>H<sub>2f</sub>-cycloC₆H₁₀—C<sub>g</sub>H<sub>2g</sub>—    (IV)

wherein f and g are independently from 1 to 6,
(vii) a grouping of formula V

-3(4),8(9)-di(methylene)-tricyclo [5.2.1.0²·⁶]-decane-    (V)

(viii) a grouping of formula VI

—C<sub>m</sub>H<sub>2m</sub>—(OC<sub>n</sub>H<sub>2n</sub>)<sub>p</sub>—C<sub>q</sub>H<sub>2q</sub>—    (VI)

wherein m is 1 to 4, n is 2 to 4, p is 1 to 20, q is 1 to 4 and wherein, optionally, the alkoxide units are mixed alkoxide units, in any arbitrary sequence are present in the group;

by:
(1) reacting an olefinic substrate having hydrocarbyl groups with at least two double bonds with an organic hydroperoxide to form an oxirane ring,
(2) opening said oxirane ring with an alcohol in the presence of a molybdenum compound as a first catalyst component and a second catalyst component selected from the group consisting of boron trifluoride, an alumina, 1,8-diazabicyclo-(5.4.0)-undec-7-ene, and 1,4-diazabicyclo-(2.2.2)-octane, and
(3) preparing the amphiphilic compounds by
(3.1) alkoxylating the hydroxyethers with an alkoxylating agent to yield an amphiphilic nonionic compound, or
(3.2) reacting the hydroxyethers to form an amphiphilic ionic compound.

10. A process for preparing amphiphilic compounds as claimed in claim 9, wherein the preparation of the amphiphilic ionic compound according to (3.2) is carried out by reaction of the hydroxyethers in accordance with one of the following steps:
(a) reaction of the hydroxyethers with an oxirane selected from the group consisting of sulfur trioxide/inert gas, oleum, chloro-sulfonic acid, sulfamic acid, phosphoric acid, and oxygen in the presence of a derivative selected from the group consisting of 2,2',6,6'-tetramethylpiperidine oxide, a halo-acetic acid, a sultone, a taurine, maleic anhydride, and sodium bisulfide, or
(b) alkoxylation followed by step (a).

11. A process as claimed in claim 9 or 10, wherein the reaction is carried out as a one-pot reaction.

12. A process as claimed in claim 9 or 10, wherein a solvent selected from the group consisting of a monohydric or polyhydric alcohol is present.

13. A process as claimed in claim 9 or 10, wherein water is excluded.

14. A process as claimed in claim 9 or 10, wherein said molybdenum compound is soluble in the reaction mixture.

15. A process as claimed in claim 9 or 10, wherein said molybdenum compound is MoO₂(acac)₂ or Mo(CO)₆.

16. A process as claimed in claim 9 or 10, wherein said molybdenum compound is molybdenum oxide on a catalyst carrier.

17. A process as claimed in claim 9 or 10, wherein R² is a branched or unbranched hydrocarbon group.

18. A process as claimed in claim 9 or 10, wherein R² contains from 0 to 10 oxygen atoms.

19. A process as claimed in claim 9, wherein step (3.2) is followed by a neutralization step.

20. A process as claimed in claim 9, wherein said alcohol is a monohydric alcohol.

21. A process as claimed in claim 10, wherein step (a) is followed by a neutralization step.

* * * * *